United States Patent [19]

Mackenroth et al.

[11] Patent Number: 5,206,442
[45] Date of Patent: Apr. 27, 1993

[54] MANUFACTURING OF α,β-UNSATURATED ALDEHYDES AND KETONES

[75] Inventors: Christiane Mackenroth, Bad Durkheim; Ernst Buschmann, Ludwigshafen, both of Fed. Rep. of Germany

[73] Assignee: BASF Aktiengesellschaft, Ludwigshafen, Fed. Rep. of Germany

[21] Appl. No.: 835,552

[22] Filed: Feb. 14, 1992

[30] Foreign Application Priority Data

Mar. 5, 1991 [DE] Fed. Rep. of Germany ....... 4106908

[51] Int. Cl.$^5$ ............................................. C07C 45/60
[52] U.S. Cl. ..................................... 568/447; 568/483; 568/405; 568/442; 568/420; 568/386; 568/361; 568/322; 560/262
[58] Field of Search ............... 568/486, 442, 447, 483, 568/405, 452, 420, 386, 361, 322; 560/262

[56] References Cited

U.S. PATENT DOCUMENTS

| | | | |
|---|---|---|---|
| 3,453,317 | 7/1969 | Marbet et al. | 568/405 |
| 3,928,459 | 12/1975 | Mercier | 568/486 |
| 3,953,518 | 4/1976 | Wehrli | 568/405 |
| 4,626,601 | 12/1986 | Fuchs et al. | 568/442 |

FOREIGN PATENT DOCUMENTS

| | | | |
|---|---|---|---|
| 56-139437 | 10/1981 | Japan | 568/386 |
| 60-190730 | 9/1985 | Japan | 568/386 |
| 63-250340 | 10/1988 | Japan | 568/483 |

OTHER PUBLICATIONS

Bauduin et al., Tetrahedron, vol. 33, pp. 3105–3109 (1977).
Morrison et al., "Organic Chemistry", pp. 641–643 (1966).
Synthesis, Jul. 1981, pp. 501–522, F. A. J. Meskens, "Methods for the Preparation of Acetals' from Alcohols or Oxiranes and Carbonyl Compounds".
W. Theilheimer, vol. 4, 1966, "Synthetic Methods of Organic Chemistry".
Houben-Weyl, vol. VI/3, 1965, "Methoden Der Organischen Chemie", pp. 253–254.
"Protective Groups in Organic Synthesis", T. W. Greene, p. 126.
Methoden Der Organischen Chemie, Houben-Weyl, vol XII/1, 1954 pp. 434–441, "Sauerstoff-Verbindungen II-Teil1: Aldehyde".
International Journal of Methods of Synthesis Organic Chemistry, pp. 132–133, Stowell, et al., "Synthesis 1979".
Methoden Der Organischen Chemie, Houben-Weyl, vol. VI/3, 1965, pp. 278–281, "Sauerstoff-Verbindungen I-Teil3".

*Primary Examiner*—James H. Reamer
*Attorney, Agent, or Firm*—Oblon, Spivak, McClelland, Maier & Neustadt

[57] ABSTRACT

The preparation of α,β-unsaturated aldehydes and ketones I $$O=C(R^1)-CR^2=CR^3R^4 \qquad \text{I}$$

is carried out by acid hydrolysis of cyclic α,β-unsaturated acetals II

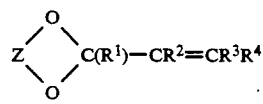

in the presence of saturated aldehydes.

7 Claims, No Drawings

MANUFACTURING OF α,β-UNSATURATED ALDEHYDES AND KETONES

The present invention relates to a novel process for the preparation of an α,β-unsaturated aldehyde or ketone of the general formula I

$$O=C(R^1)-CR^2=CR^3R^4 \qquad I,$$

in which the substituents $R^1$, $R^2$, $R^3$, and $R^4$ independently denote hydrogen, optionally substituted alkyl, or optionally substituted aryl, by acid hydrolysis of the corresponding cyclic α,β-unsaturated acetal of the general formula II

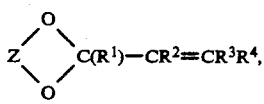

in which Z stands for an optionally substituted carbon chain having from 2 to 3 carbon atoms.

It is known from the literature that acetals can be converted to the corresponding aldehydes by acid hydrolysis (Houben-Weyl, *Methoden der Organischen Chemie*, Vol. XII/1, pp. 434 et seq.). This conversion is not quantitative and must therefore be repeated a number of times. As a result, considerable losses of target product occur in the case of thermally unstable compounds, e.g. α,β-unsaturated compounds.

A method of producing β,γ-unsaturated aldehydes is also known in which a corresponding cyclic acetal is first of all reacted with methanol in acidic medium to form the dimethyl acetal, which is then quantitatively hydrolyzed in conventional manner (Stowell, *Synthesis* 1979, pp. 132 et seq.). If this method is carried out on α,β-unsaturated acetals, the result is a complex mixture of products.

In another process described in the literature aldehydes and ketones are produced from the corresponding acetals by acid hydrolysis in the presence of acetone (Houben-Weyl, *Methoden der Organischen Chemie*, Vol. VI/3, pp. 278 et seq.). When this process is applied to α,β-unsaturated acetals, there is no complete conversion of the starting materials.

It is an object of the present invention to provide a simple and economical process for the manufacture of α,β-unsaturated aldehydes and ketones.

Accordingly, we have found a process for the preparation of an α,β-unsaturated aldehyde or ketone of the general formula I

$$O=C(R^1)-CR^2=CR^3R^4 \qquad I,$$

in which the substituents $R^1$, $R^2$, $R^3$, and $R^4$ independently denote hydrogen, optionally substituted alkyl, or optionally substituted aryl, by acid hydrolysis of the corresponding cyclic α,β-unsaturated acetal of the general formula II

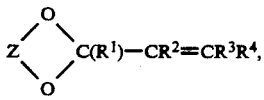

in which Z stands for an optionally substituted carbon chain having from 2 to 3 carbon atoms, wherein the hydrolysis is carried out in the presence of a saturated aldehyde.

Compared with the processes of the prior art, our novel process provides considerably improved yields of product.

Saturated aldehydes suitable for use in splitting acetals in accordance with the present invention are, in particular, aliphatic aldehydes. Knowledge gained hitherto has shown that the process is in no way affected by the length of the carbon chain of the aldehyde or by the extent to which its carbon chain is branched or by the presence of substituents which are inert under the conditions of the reaction, such as alkoxy groups or alkylcarbonyl groups.

In general, the type of saturated aldehyde to be used will depend on the following factors:

the aldehyde should be readily available;

the aldehyde must not, under the hydrolysis conditions, react with the target product present in the reaction medium;

the aldehyde must not, under the hydrolysis conditions, convert to a product which is difficult to separate from the target product.

Taking these points into consideration, it will be usual to use unbranched or branched $C_1$-$C_6$-aldehydes such as formaldehyde, acetaldehyde, propionaldehyde, butyraldehyde, α-methyl propionaldehyde, pentanal, α-methyl butyraldehyde, β-methyl butyraldehyde, α,α-dimethyl propionaldehyde, hexanal, α-methyl pentanal, β-methyl pentanal, α-methyl pentanal, α,α-dimethyl butyraldehyde, α,β-dimethyl butyraldehyde, β,β-dimethyl butyraldehyde, and α-ethyl butyraldehyde, preferably unbranched $C_3$-$C_5$-aldehydes and especially propionaldehyde.

The amount of saturated aldehyde used will generally be at least equimolar to compound II, since it is consumed in molar quantities according to the reaction equation. The amount of saturated aldehyde used will normally be from 1 to 3 molar equivalents, preferably from 1 to 2 molar equivalents and more preferably from 1 to 1.2 molar equivalents, based on compound II. As far as we know, the use of a larger excess of saturated aldehyde has no additional benefit on the process.

The process of the invention is generally carried out in an inert aprotic organic solvent in the presence of an acid, as in prior art processes for splitting acetal (hydrolysis).

The reaction is carried out at a temperature of from 0° to 150° C., preferably from 20° to 100° C. and more preferably from 50° to 70° C.

Suitable solvents are aliphatic hydrocarbons such as pentane, hexane, cyclohexane, and petroleum ether, aromatic hydrocarbons such as toluene, o-, m-, and p-xylenes, halohydrocarbons such as methylene chloride, chloroform, and chlorobenzene, ethers such as diethyl ether, diisopropyl ether, t-butylmethyl ether, dioxane, anisol, and tetrahydrofuran, nitriles such as acetonitrile and propionitrile, ketones such as acetone, methylethyl ketone, diethyl ketone, and t-butylmethyl ketone, and dimethyl sulfoxide and dimethyl formamide. Tetrahydrofuran is particularly preferred.

The said solvents may also be used in admixture with each other.

Acids and acid catalysts which may be used comprise inorganic acids such as hydrofluoric acid, hydrochloric acid, hydrobromic acid, sulfuric acid, and perchloric acid, Lewis acids such as boron trifluoride, aluminum trichloride, iron(III) chloride, tin(IV) chloride, titanium(IV) chloride, and zinc(II) chloride, and organic acids such as formic acid, acetic acid, propionic acid, oxalic acid, citric acid, and trifluoroacetic acid.

These acids are generally used in catalytsc amounts. They are advantageously used in an amount of from 0.1 to 1 molar equivalent, preferably from 0.2 to 0.8 molar equivalent and more preferably from 0.4 to 0.6 molar equivalent, based on the acetal II used.

The reaction mixture is worked up, and the product isolated, in conventional manner, i.e. by removing the acid from the reaction mixture and then isolating the product from the resulting reaction solution by crystallization, chromatography, or distillation.

The process of the invention is suitable for the preparation of α,β-unsaturated aldehydes or ketones I and substituted derivatives of the corresponding α,β-unsaturated acetals II, particularly those of the general formula IIa

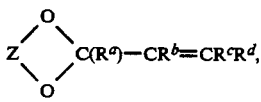

in which the substituents have the following meanings:
$R^a$, $R^b$, $R^c$, and $R^d$ are independently hydrogen or carbo-organic radicals such as alkyl, alkenyl, alkynyl, or aryl; as far as is known, the process is not impaired when these carbo-organic radicals carry substituents which are inert to the conditions of the reaction.

Preferred meanings of the radicals $R^a$, $R^b$, $R^c$, and $R^d$ are as follows:

hydrogen;

alkyl groups of up to 20 carbon atoms, in particular $C_1$–$C_4$-alkyl groups such as methyl, ethyl, propyl, 1-methylethyl, butyl, 1-methylpropyl, and 2-methylpropyl;

alkenyl groups of up to 20 carbon atoms, in particular $C_2$–$C_4$-alkenyl groups such as ethenyl, 1-propenyl, 2-propenyl, 1-methylethenyl, 1-butenyl, 2-butenyl, 3-butenyl, 1-methyl-1-propenyl, 1-methyl-2-propenyl, 2-methyl-1-propenyl, and 2-methyl-2-propenyl;

alkynyl groups of up to 20 carbon atoms, in particular $C_2$–$C_4$-alkynyl groups such as ethynyl, 1-propynyl, 2-propynyl, 1-butynyl, 2-butynyl, 3-butynyl, and 1-methyl-2-propynyl; and aryl groups such as, in particular, phenyl.

The aforementioned radicals may themselves be interrupted by hetero atoms such as nitrogen, oxygen, and sulfur, or they may carry further inert radicals such as halogen, nitro, sulfonyl, arylsulfonyl, carboxyl, cycloalkyl, or cycloalkenyl.

Z stands for an optionally substituted $C_2$ or $C_3$ chain, in particular

—CH$_2$—C(CH$_3$)$_2$—CH$_2$—

The now more readily available α,β-unsaturated aldehydes or ketones I of the invention and their derivatives serve, for example, as intermediates for the synthesis of pharmaceuticals, paints and plant protectants.

When used as intermediates for the synthesis of plant protectants, the α,β-unsaturated aldehydes or ketones preferably have the formula Ia

 Ia, in which the substituents have the following meanings:
$R^a$, $R^b$, $R^c$, and $R^d$ are independently hydrogen;

$C_1$–$C_{20}$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2-methylpropyl.

These compounds Ia may be obtained, for example, by converting the acetal of an α-bromine carbonyl compound of the general formula IIIa to the corresponding triphenylphosphonium salt IVa in known manner using triphenylphosphine, reacting the resulting salt in resulting salt in known manner with an aldehyde or ketone of the general formula Va as a Wittig reaction, and then splitting the resulting α,β-unsaturated acetal IIa to form the α,β-unsaturated aldehyde or ketone Ia in accordance with the present invention:

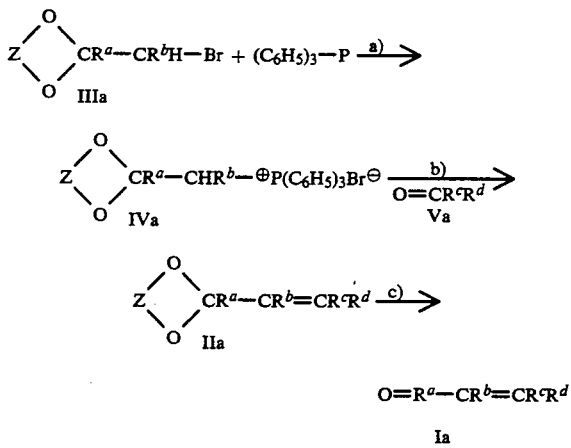

The reactions a), b) and c) are carried out as follows:

a) Phosphonium salt synthesis (Sargent et al., J.Chem.Soc., Pt 1, 1974, 37 et seq.)

The reaction is generally carried out at a temperature of from 100° to 200° C. and preferably from 100° to 160° C.

Suitable solvents are, for example, toluene, o-, m-, and p-xylenes, and dimethyl formamide, preferably toluene.

b) Wittig reaction (Sargent et al., J.Chem.Soc., Pt 1, 1974, 37 et seq.)

The reaction is generally carried out at a temperature of from 20° to 100° C. and preferably from 20° to 30° C.

Examples of suitable solvents are those mentioned above, particularly dimethyl formamide.

c) Acetal cleavage

This takes place in accordance with the process of the invention described above.

The α,β-unsaturated aldehydes or ketones of the general formula Ia may be used for the synthesis of pesticides and especially for the synthesis of pheromones. To this end, they are converted to the dienes VI in known manner, these being known to act as sex baits on certain lepidoptera species.

This synthesis is illustrated diagrammatically by the following reaction equation:

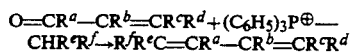
$$O=CR^a—CR^b=CR^cR^d + (C_6H_5)_3P^\oplus—CHR^eR^f \rightarrow R^fR^eC=CR^a—CR^b=CR^cR^d$$

Active substances of this kind are described in DE-A 3,817,399.

In addition, the α,β-unsaturated aldehydes or ketones of the general formula I may be used for the synthesis of carotenoids in which the substituents have the following meanings:

Z: Ethylene or propylene radical optionally substituted by $C_1$–$C_4$-alkyl, preferably methyl;

$R^1$, $R^2$, and $R^3$: Hydrogen or $C_1$–$C_4$-alkyl:
$R^1$: preferably H;
$R^2$: preferably H or —$CH_3$;
$R^3$: preferably H or —$CH_3$;
$R^4$: Polyene chain containing from 4 to 20 carbon atoms, optionally substituted by $C_1$–$C_4$-alkyl, preferably methyl, or by the group

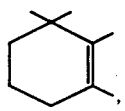

in which the cyclohexene ring may additionally carry oxygen functions such as an oxo group and/or an alkoxy group or hydroxyl group, preferred meanings being:

$R^1$ = H $R^2$ = H or —$CH_3$ $R^3$ = H or —$CH_3$ $R^4$ = 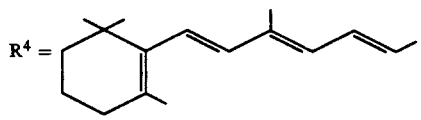

EXPERIMENTAL SECTION

Example 1

Preparation of Cinnamaldehyde

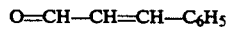
$$O=CH—CH=CH—C_6H_5$$

To a solution of 10 g (46 mmoles) of cinnamaldehyde-neopentylacetal in 20 ml of tetrahydrofuran there were added, at 25° C., 1.67 g (46 mmoles) of 10% hydrochloric acid followed by 2.67 g (46 mmoles) of propionaldehyde. The reaction mixture was stirred for 20 hours at 25° C., and water was then added. The product was isolated from the organic phase by extraction with t-butylmethyl ether.

There were obtained 7.2 g of crude product containing 72.4% of cinnamaldehyde as determined by gas-chromatographic analysis (yield 86%).

Example 2

Preparation of Cinnamaldehyde

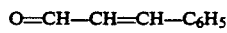
$$O=CH—CH=CH—C_6H_5$$

Example 1 was repeated but without the use of propionaldehyde. There were obtained 9 g of crude product containing 38.5% of cinnamaldehyde as determined by gas-chromatographic analysis (yield 57%). This crude product also contained 50.9% of unconverted cinnamaldehyde-neopentylacetal.

Example 3

Preparation of 3-[4-(1,1-dimethylethyl)-phenyl]-2-methylpropenal

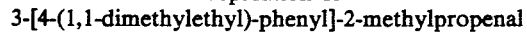
$$O=CH—C(CH_3)=CH—[4—C(CH_3)_3]—C_6H_4$$

To a solution of 28.8 g (100 mmoles) of 3-[4-(1,1-dimethylethyl)-phenyl]-2-methylpropenal-neopentylacetal in 100 ml of tetrahydrofuran there were added, at 25° C., 3.65 g (10 mmoles) of 10% hydrochloric acid followed by 5.8 g (100 mmoles) of propionaldehyde. The reaction mixture was stirred for 3 hours at 60° C. and then worked up as described in Example 1. There were obtained 23 g of crude product containing 79.8% of 3-[4-(1,1-dimethylethyl)-phenyl]-2-methylpropenal, as determined by gas-chromatographic analysis (yield 91%).

Example 4

Preparation of 3-[4-(1,1-dimethylethyl)-phenyl]-2-methylpropenal

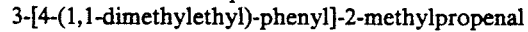
$$O=CH—C(CH_3)=CH—[4-C(CH_3)_3]—C_6H_4$$

Example 3 was repeated except that no propionaldehyde was used. There were obtained 19.5 g of crude product containing 54.5% of 3-[4-(1,1-dimethylethyl)-phenyl]-2-methyl-propenal, as determined by gas-chromatographic analysis (yield 66%). This crude product also contained 20.0% of unconverted 3-[4-1,1-dimethylethyl)-phenyl]-2-methyl-propenal-neopentylacetal.

Example 5

Preparation of 9-acetoxynonenal and 9-hydroxynonenal

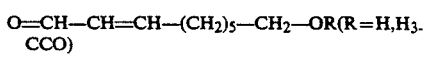
$$O=CH—CH=CH—(CH_2)_5—CH_2—OR(R=H, H_3CCO)$$

A mixture of 144.1 g (0.55 mole) of triphenylphosphine, 118.6 g (0.55 mole) of 2-bromomethyl-5,5-dimethyl-1,3-dioxane (96.9% strength) 200 ml of xylene, and 200 ml of dimethyl formamide was stirred for 8 hours at 130° C. After the reaction mixture had been allowed to cool to 25° C., 67.2 g (0.6 mole) of potassium t-butylate were added thereto. The mixture was stirred for 2 hours at 25° C., after which 90.5 g (0.5 mole) of 7-acetoxyheptanal (95% strength) were mixed therewith. The resulting reaction mixture was stirred overnight (15 hours) at 25° C.

To this mixture there were then added, at 25° C., 91.3 g (0.25 mole) of 10% hydrochloric acid followed by 29 g (0.5 mole) of propionaldehyde. The reaction mixture was stirred for 4 hours at 60° C. and then worked up as described in Example 1. There were thus obtained 145 g of crude product containing 31.0% of 9-acetoxynonenal and 7.7% of 9-hydroxynonenal, as determined by gas-chromatographic analysis (total yield of target products 60%).

Example 6

Preparation of 9-acetoxynonenal and 9-hydroxynonenal

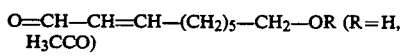
O=CH—CH=CH—(CH$_2$)$_5$—CH$_2$—OR (R=H, H$_3$CCO)

Example 5 was repeated except that no propionaldehyde was used and 219 g (0.6 mole) of 10% hydrochloric acid were used in the presence of 145 g (2.5 moles) of acetone, to give 86 g of crude product containing 8.8% of 9-acetoxynonenal and 13.5% of 9-hydroxynonenal (total yield of target products 23%). This crude product also contained 12.1% of unconverted 9-hydroxynonenal-neopentylacetal.

Examples 7 to 10

Preparation of 9-acetoxynonenal

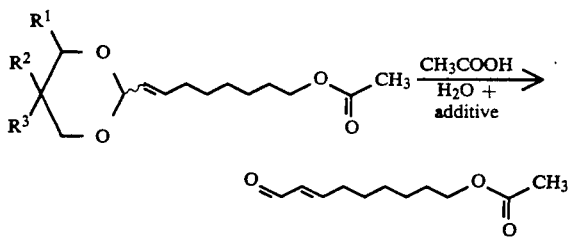

To 72 g of acetic acid in 100 g of water there were added 0.25 mole of acetal and 0.3 mole of additive. The mixture was refluxed for 1 hour and cooled. 500 ml of toluene were added, and the aqueous phase was separated and neutralized by washing with saturated NaHCO$_3$ solution. The solution was evaporated down to give crude products of the following compositions:

| Additive | R$^1$ | R$^2$ | R$^3$ | Acetal | Aldehyde |
|---|---|---|---|---|---|
| none | H | CH$_3$ | CH$_3$ | 12.6% | 87.4% |
| acetone | H | CH$_3$ | CH$_3$ | 8.8% | 91.2% |
| propionaldehyde | H | CH$_3$ | CH$_3$ | 4.0% | 96.0% |
| propionaldehyde | CH$_3$ | H | H | 4.2% | 95.8% |

Example 11

Preparation of Retinal

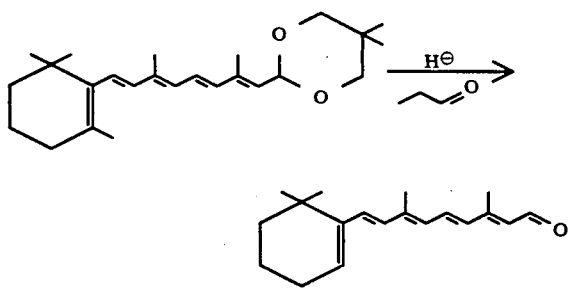

To a solution of 0.25 mole of retinal-neopentylglycolacetal in 300 ml of heptane there were added, with stirring, 100 ml of 2% sulfuric acid, 150 ml of isopropanol, and 17.4 g (0.3 mole) of propanol, and stirring was continued for 2 hours at 65° C. The acetal content as determined by HPLC was below 1%. The resulting retinal was present in a mixture of a number of stereoisomers. The proportions of the stereoisomers (all trans, 9-cis, 11-cis, 13-cis, and di-cis) depend on the starting material and on the duration of hydrolysis. Acid and a higher temperature isomerize until a final state of equilibrium of the stereoisomers is reached. The mixture is worked up by adding 250 ml of water in order to reduce the solubility of retinal in the isopropanol/water phase. The bottom phase is removed to give retinal dissolved in heptane (yield 97%).

We claim:

1. A process for the preparation of an α,β-unsaturated aldehyde or ketone of the formula I $$O=C(R^1)—CR^2=CR^3R^4 \qquad I,$$

in which the substituents R$^1$, R$^2$, R$^3$, and R$^4$ independently denote hydrogen, alkyl, substituted alkyl, aryl, or substituted aryl, by acid hydrolysis of the corresponding cyclic α,β-unsaturated acetal or ketal of the formula II $$Z\begin{matrix}O\\ \\O\end{matrix}C(R^1)—CR^2=CR^3R^4, \qquad II$$

in which Z stands for an unsubstituted or substituted carbon chain having 2 to 3 carbon atoms, wherein the substituted alkyl, substituted aryl, or substituted carbon chain may be interrupted by heteroatoms, such as nitrogen, oxygen, and sulfur, or substituted with radicals, such as halogen, nitro, sulfonyl, arylsulfonyl, carboxyl, cycloalkyl, or cycloalkenyl, wherein the hydrolysis is carried out in the presence of a saturated aldehyde, wherein the saturated aldehyde is used in an amount of 1 to 3 molar equivalents, based on the amount of cyclic α,β-unsaturated acetal or ketal of the formula II used, and wherein the hydrolysis is carried out at a temperature from 0° to 150° C.

2. A process as claimed in claim 1, wherein Z stands for a 1,3-(2,2-dimethyl)-propylene chain.

3. A process as claimed in claim 1, wherein the saturated aldehyde used is an unbranched or branched C$_1$–C$_6$-aldehyde.

4. A process as claimed in claim 1, wherein the hydrolysis is carried out in an inert organic solvent.

5. A process as claimed in claim 3, wherein the hydrolysis is carried out in an aprotic solvent.

6. A process as claimed in claim 1, wherein the hydrolysis is carried out using a lower carboxylic acid or a mineral acid.

7. A process as claimed in claim 1, wherein the hydrolysis is carried out using a catalytic amount of a lower carboxylic acid or mineral acid.

* * * * *